United States Patent [19]
He

[11] Patent Number: 6,100,255
[45] Date of Patent: Aug. 8, 2000

[54] 3-AMINOALKYLAMINO-2H-1,4-BENZOXAZINES AND 3-AMINOALKYLAMINO-2H-1,4-BENZOTHIAZINES: DOPAMINE RECEPTOR SUBTYPE SPECIFIC LIGANDS

[75] Inventor: Xiao-shu He, Branford, Conn.

[73] Assignee: Neurogen Corporation, Branford, Conn.

[21] Appl. No.: 09/181,624

[22] Filed: Oct. 28, 1998

Related U.S. Application Data

[60] Provisional application No. 60/063,923, Oct. 31, 1997.

[51] Int. Cl.[7] ............... C07D 413/12; C07D 417/12; A61K 31/496; A61K 31/5355
[52] U.S. Cl. ............... 514/224.2; 544/51; 544/105; 514/230.5
[58] Field of Search ............ 544/105, 51; 514/224.2, 514/230.5

[56] References Cited

FOREIGN PATENT DOCUMENTS

WO 9923092  5/1999  WIPO.

OTHER PUBLICATIONS

He et al., Bioorg.&Medicinal Che. Lett., A New Series of Selective Dopamine D4,7(18),pp. 2399–2402, Sep. 23, 1997.

Primary Examiner—Mukund J. Shah
Assistant Examiner—Sudhaker B. Patel
Attorney, Agent, or Firm—McDonnell Boehnen Hulbert & Berghoff; Steve Sarussi

[57] ABSTRACT

Disclosed are compounds of the formula:

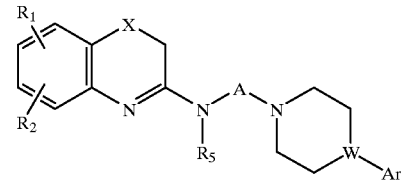

or the pharmaceutically acceptable acid addition salts thereof,
wherein:
 Ar represents aryl or heteroaryl;
 $R_1$ and $R_2$ are the same or different and represent organic or inorganic substituents;
 $R_5$ is hydrogen or $C_1$–$C_6$ alkyl;
 W represents CH or nitrogen;
 X is oxygen or sulfur; and
 A represents an alkylene group,
which compounds bind selectively with high affinity to the dopamine $D_4$ receptor subtype and are therefore of use in treatment of various neuropsychological disorders.

29 Claims, No Drawings

3-AMINOALKYLAMINO-2H-1,4-BENZOXAZINES AND 3-AMINOALKYLAMINO-2H-1,4-BENZOTHIAZINES: DOPAMINE RECEPTOR SUBTYPE SPECIFIC LIGANDS

This is a continuation-in-part of application Ser. No. 60/063,923, filed Oct. 31, 1997.

BACKGROUND OF THE INVENTION

1. Field of the Invention

This invention relates to certain 3-aminoalkylamino-2H-1,4-benzoxazines and 3-aminoalkylamino-2H-1,4-benzothiazines and pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Nature, 347: 146, Sokoloff et al., 1990; Nature, 350: 610, Van Tol et al., 1991). Its unique localization in limbic brain areas and its differential recognition of various antipsychotics indicates that the $D_4$ receptor plays a major role in the etiology of schizophrenia. Selective $D_4$ antagonists are considered effective antipsychotics free from the neurological side effects displayed by conventional neuroleptics.

SUMMARY OF THE INVENTION

This invention provides novel compounds which interact with dopamine subtypes. Accordingly, in a broad aspect, the invention provides compounds of Formula I:

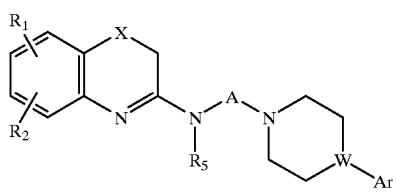

I or the pharmaceutically acceptable acid addition salts thereof, wherein:

Ar represents aryl or heteroaryl of the formula

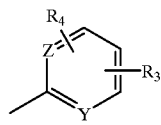

where Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, cycloalkoxy, alkylthio, hydroxy, amino, mono- or dialkylamino where each alkyl is $C_1$–$C_6$ alkyl, cyano, nitro, trifluoromethyl or trifluoromethoxy; or $R_3$ and $R_4$ together represent a $C_1$–$C_2$ alkylene dioxy group or a $C_1$–$C_3$ alkylene oxy group;

$R_5$ is hydrogen or $C_1$–$C_6$ alkyl;

W represents CH or nitrogen;

X is oxygen or sulfur; and

A represents an alkylene group of 2 to 5 carbon atoms, each of which carbon atoms is optionally substituted with one or two alkyl groups having from 1 to 4 carbon atoms.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neurospychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Thus, in another aspect, the invention provides methods for treatment and/or prevention of neuropsychochological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of memory-impairment or Alzheimer's disease by modulation of $D_4$ receptors which selectively exist in limbic area known to control emotion and cognitive functions. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

DETAILED DESCRIPTION OF THE INVENTION

The compounds of Formula I can be used in in the treatment of affective disorders such as schizophrenia, depression, Alzheimer's disease and certain movement disorders such as Parkinsonism and dystonia. Furthermore compounds of this invention can be used in treating the extrapyramidal side effects associated with the use of conventional neuroleptic agents. The compounds of the present invention are also useful for the treatment of other disorders which respond to dopaminergic blockade such as substance abuse and obsessive compulsive disorder.

As mentioned above, the invention encompasses 3-aminoalkylamino-2H-1,4-benzoxazines and 3-aminoalkylamino-2H-1,4-benzothiazines of Formula I. Preferred compounds of Formula I are those where $R_1$ and $R_2$ are hydrogen, and A is alkylene of from 2–4 carbon atoms.

In addition to compounds of general Formula I described above, the invention encompasses compounds of Formula IA:

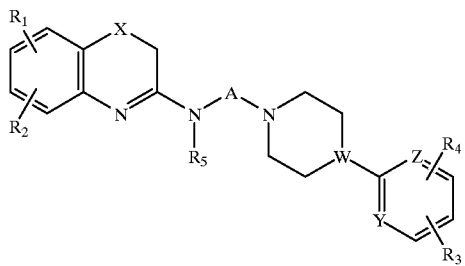

IA wherein:

Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, alkylthio, hydroxy, amino, mono- or dialkylamino where each alkyl is $C_1$–$C_6$ alkyl, cyano, nitro, trifluoromethyl or trifluoromethoxy;

$R_5$ is hydrogen or $C_1$–$C_6$ alkyl;

W represents CH or nitrogen;

X is oxygen or sulfur; and

A represents an alkylene group of 2 to 5 carbon atoms each of which carbon atoms is optionally substituted with one or two alkyl groups having from 1 to 4 carbon atoms.

Preferred compounds of Formula IA are those where Z and Y are both nitrogen. More preferably, W, Y and Z are all nitrogen. Other preferred compounds of Formula IA are those where $R_1$ and $R_2$ are hydrogen and $R_5$ is hydrogen, methyl, or ethyl.

The present invention also provides compounds of Formula IB:

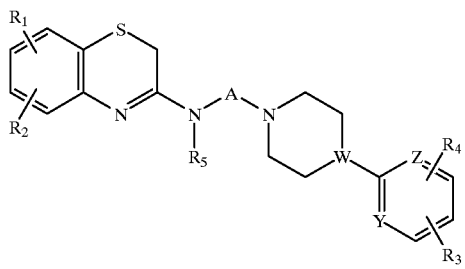

IB wherein:

Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, alkylthio, hydroxy, amino, mono- or dialkylamino where each alkyl is $C_1$–$C_6$ alkyl, cyano, nitro, trifluoromethyl or trifluoromethoxy;

$R_5$ is hydrogen or $C_1$–$C_6$ alkyl;

W represents CH or nitrogen; and

A represents an alkylene group of 2 to 5 carbon atoms each of which carbon atoms is optionally substituted with one or two alkyl groups having from 1 to 4 carbon atoms.

Preferred compounds of Formula IB are those where Z and Y are both nitrogen. More preferred compounds of Formula IB are where W, Y and Z are nitrogen and $R_5$ is hydrogen, methyl, or ethyl. Particularly preferred compounds of Formula IB are where W, Y and Z are nitrogen, $R_5$ is hydrogen, methyl, or ethyl, and $R_1$ and $R_2$ are both hydrogen.

The invention further provides compounds of Formula IC.

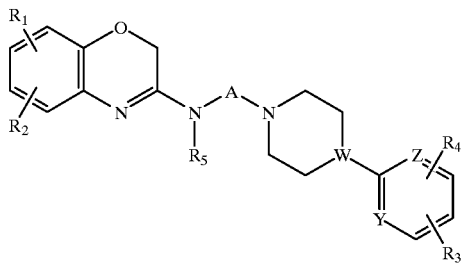

IC wherein:

Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, alkylthio, hydroxy, amino, mono- or dialkylamino where each alkyl is $C_1$–$C_6$ alkyl, cyano, nitro, trifluoromethyl or trifluoromethoxy;

$R_5$ is hydrogen or $C_1$–$C_6$ alkyl;

W represents CH or nitrogen; and

A represents an alkylene group of 2 to 5 carbon atoms each of which carbon atoms is optionally substituted with one or two alkyl groups having from 1 to 4 carbon atoms.

Preferred compounds of Formula IC are those where Z and Y are both nitrogen. More preferred compounds of Formula IC are where W, Y and Z are nitrogen and $R_5$ is hydrogen, methyl, or ethyl. Particularly preferred compounds of Formula IC are where W, Y and Z are nitrogen, $R_5$ is hydrogen, methyl, or ethyl, and $R_1$ and $R_2$ are both hydrogen.

The invention further encompasses compounds of Formula II:

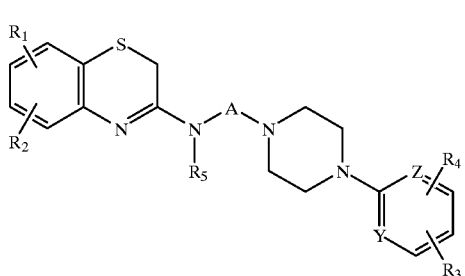

II wherein:

Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, alkylthio, hydroxy, amino, mono- or dialkylamino where each alkyl is $C_1$–$C_6$ alkyl, cyano, nitro, trifluoromethyl or trifluoromethoxy;

$R_5$ is hydrogen or $C_1$–$C_6$ alkyl; and

A represents an alkylene group of 2 to 5 carbon atoms each of which carbon atoms is optionally substituted with one or two alkyl groups having from 1 to 4 carbon atoms.

Preferred compounds of Formula II are those where Z and Y are both nitrogen. More preferred compounds of Formula II are where Y and Z are nitrogen and $R_5$ is hydrogen, methyl, or ethyl. Particularly preferred compounds of Formula II are where Y and Z are nitrogen, $R_5$ is hydrogen, methyl, or ethyl, $R_1$, $R_2$ and $R_4$ are hydrogen.

In addition, the invention provides compounds of Formula IIA:

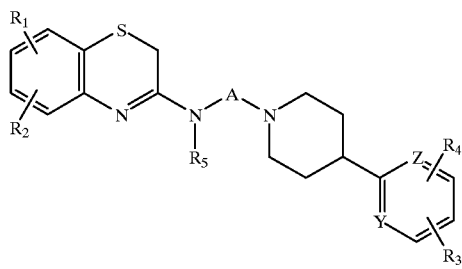

IIA

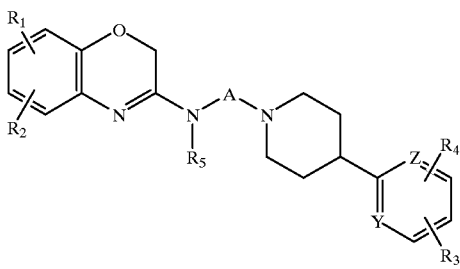

IIIA wherein:

Y and Z independently represent CH or nitrogen;

$R_1$, $R_2$, $R_3$ and $R_4$ are the same or different and represent hydrogen, halogen, $C_1-C_6$ alkyl, $C_1-C_4$ alkoxy, alkylthio, hydroxy, amino, mono- or dialkylamino where each alkyl is $C_1-C_6$ alkyl, cyano, nitro, trifluoromethyl or trifluoromethoxy;

$R_5$ is hydrogen or $C_1-C_6$ alkyl; and

A represents an alkylene group of 2 to 5 carbon atoms each of which carbon atoms is optionally substituted with one or two alkyl groups having from 1 to 4 carbon atoms.

Preferred compounds of Formula IIA are those where Z and Y are both nitrogen. More preferred compounds of Formula IIA are where Y and Z are nitrogen and $R_5$ is hydrogen, methyl, or ethyl. Particularly preferred compounds of Formula IIA are where Y and Z are nitrogen, $R_5$ is hydrogen, methyl, or ethyl, $R_1$, $R_2$ and $R_4$ are hydrogen.

Further, the present invention encompasses compounds of Formula III:

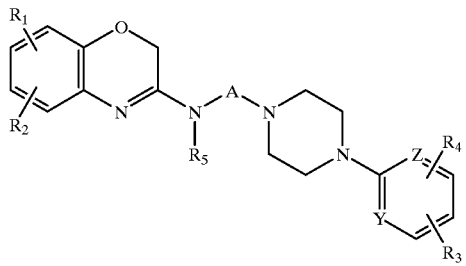

III wherein:

Y and Z independently represent CH or nitrogen;

$R_1$, $R_2$, $R_3$ and $R_4$ are the same or different and represent hydrogen, halogen, $C_1-C_6$ alkyl, $C_1-C_4$ alkoxy, alkylthio, hydroxy, amino, mono- or dialkylamino where each alkyl is $C_1-C_6$ alkyl, cyano, nitro, trifluoromethyl or trifluoromethoxy;

$R_5$ is hydrogen or $C_1-C_6$ alkyl; and

A represents an alkylene group of 2 to 5 carbon atoms each of which carbon atoms is optionally substituted with one or two alkyl groups having from 1 to 4 carbon atoms.

Preferred compounds of Formula III are those where Z and Y are both nitrogen. More preferred compounds of Formula III are where Y and Z are nitrogen and $R_5$ is hydrogen, methyl, or ethyl. Particularly preferred compounds of Formula III are where Y and Z are nitrogen, $R_5$ is hydrogen, methyl, or ethyl, $R_1$, $R_2$ and $R_4$ are hydrogen.

The invention further provides compounds of Formula IIIA:

wherein:

Y and Z independently represent CH or nitrogen;

$R_1$, $R_2$, $R_3$ and $R_4$ are the same or different and represent hydrogen, halogen, $C_1-C_6$ alkyl, $C_1-C_4$ alkoxy, alkylthio, hydroxy, amino, mono- or dialkylamino where each alkyl is A $C_1-C_6$ alkyl, cyano, nitro, trifluoromethyl or trifluoromethoxy;

$R_5$ is hydrogen or $C_1-C_6$ alkyl; and

A represents an alkylene group of 2 to 5 carbon atoms each of which carbon atoms is optionally substituted with one or two alkyl groups having from 1 to 4 carbon atoms.

Preferred compounds of Formula IIIA are those where Z and Y are both nitrogen. More preferred compounds of Formula IIIA are where Y and Z are nitrogen and $R_5$ is hydrogen, methyl, or ethyl. Particularly preferred compounds of Formula IIIA are where Y and Z are nitrogen, $R_5$ is hydrogen, methyl, or ethyl, $R_1$, $R_2$ and $R_4$ are hydrogen.

Representative Ar groups of Formula I above include the following:

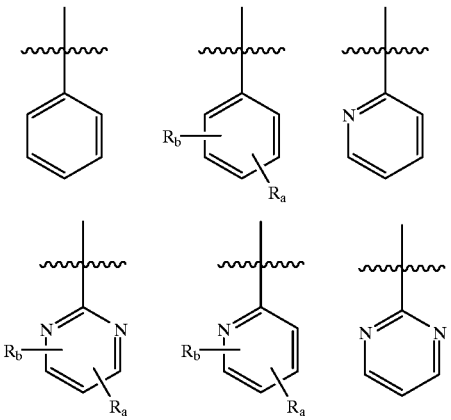

In the above Ar groups, the following definitions apply:

$R_a$ is halogen, alkyl, hydroxy, or alkoxy; and $R_b$ represents hydrogen or alkyl.

In those formulas where more than one of the same substituent appears, e.g., alkyl, those substituents are the same or different.

Preferred Ar groups of formula I above include the following:

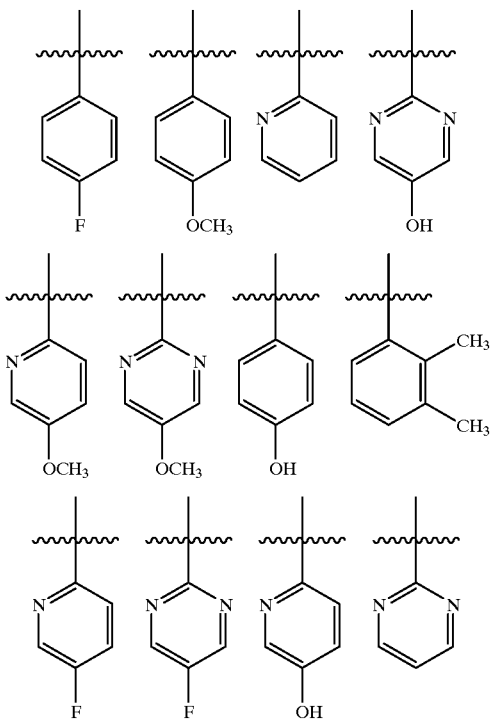

Particularly preferred Ar groups of formula I above include 5-fluoropyrimidin-2-yl and pyrimidin-2-yl.

In certain situations, the compounds of this invention I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n—ACOOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By "heteroaryl" in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl.

By "alkyl" or "lower alkyl" in the present invention is meant $C_1$–$C_6$ alkyl, i.e., straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" or "lower alkoxy" in the present invention is meant $C_1$–$C_6$ alkoxy, i.e., straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "cycloalkoxy" in the present invention is meant cycloalkylalkoxy groups having 3–7 carbon atoms where cycloalkyl is defined above.

By "$C_1$–$C_2$ alkylene dioxy group" is meant a group of the formula:

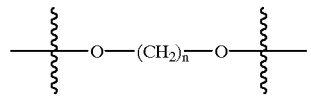

where n is 1 or 2.

By "$C_1$–$C_3$ alkylene oxy group" is meant a group of the formula:

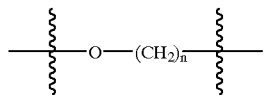

where n is 1, 2 or 3.

By halogen in the present invention is meant fluorine, bromine, chlorine, and iodine.

Representative free bases of compounds of the invention are shown below in Table 1.

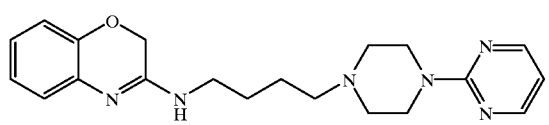

Compound 1

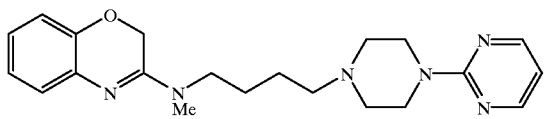

Compound 2

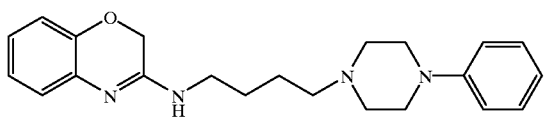

Compound 3

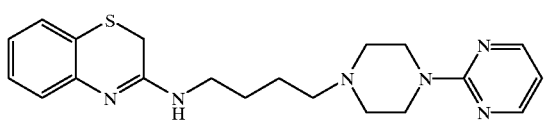

Compound 4

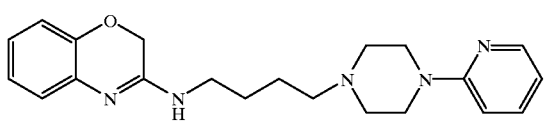

Compound 5

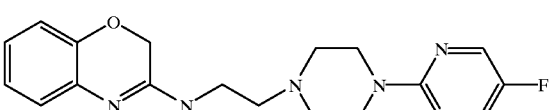

Compound 6

The compounds of the invention are useful in the treatment of neuropsychological disorders; the pharmaceutical utility of compounds of this invention is indicated by the assays for dopamine receptor subtype affinity described below in the Examples. The interaction of the compounds of the invention with dopamine receptor subtypes results in the pharmacological activities of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, a polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Representative illustrations of methods suitable for the preparation of compounds of the present invention are shown in the following Schemes. Those having skill in the art will recognize that the starting materials may be varied and additional steps employed to produce compounds encompassed by the present invention. For example, in certain situations, protection of reactive moieties such as amino groups, will be required.

Preparation Of 3-Aminoalkylamino-2H-1,4-Benzoxazines And 3-Aminoalkylamino-2H-1,4-Benzothiazines A compound of Formula I, or a pharmaceutically acceptable acid addition salt thereof may be prepared according to the reactions described generally in Scheme 1.

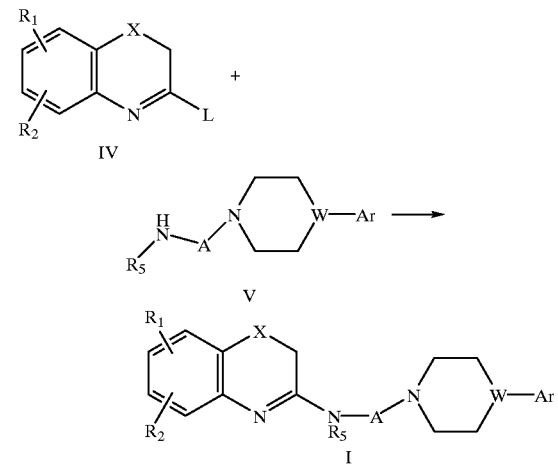

Scheme 1 wherein $R_1$, $R_2$, $R_3$, $R_4$, $R_5$, A, W, X, Y and Z are as defined above for Formula I.

As shown, a 2H-1,4-benzoxazine or 2H-1,4-benzothiazine of general structure IV, possessing an appropriate leaving group at the 3 position, may be reacted with a primary or secondary amine of general structure V in the presence of a base to afford a compound of Formula I as the desired product.

Where they are not commercially available, the compounds of general structure IV may be prepared by procedures analogous to those described in literature. Representative procedures are set forth in the examples below. The compounds of general structure V are either known or capable of being prepared by the methods known in the art. Those having skill in the art will recognize that the starting material may be varied and additional steps employed to produce compounds encompassed by the present invention.

Example 1 demonstrates the preparation of a 1-aryl-4-aminoalkylpiperazine. Example 2 provides an example of the preparation of a 2H-1,4-benzoxazine. For similar procedures can be used to synthesize 2H-1,4-benzothiazines. Example 3 demonstrates the preparation of a 3-aminoalkylamino-2H-1,4-benzoxazine. Example 4 is an example of the preparation of 3-aminoalkylamino-2H-1,4-benzothiazine.

Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The disclosures in this application of all articles and references, including patents, are incorporated herein by reference.

The invention is illustrated further by the following examples which are not to be construed as limiting the invention in scope or spirit to the specific procedures described in them.

EXAMPLE 1

Preparation of 1-(Pyrimidin-2-yl)-4-(4-aminobutyl) piperazine

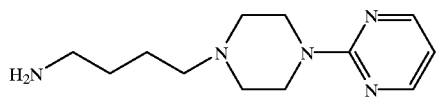

A mixture of N-(2-bromobutyl)phthalimide (18.2 g, 0.065 mole), 1-(pyrimidin-2-yl)piperazine (10.58 g, 0.0.65 mole) and potassium carbonate (17.84 g, 0.13 mole) in dimethyl formamide (150 mL) is heated at 80° C. for 16 hours under a nitrogen atmosphere. After cooling, the reaction mixture is poured into water (0.5 L) and ether (0.5 L) and the aqueous layer is then further extracted with ether (2×100 mL). The combined organic layers are dried ($Na_2SO_4$) and concentrated to provide a white solid (23.5 g, 96%, m.p. ° C.).

This solid is subsequently refluxed under nitrogen in hydrazine hydrate (100 mL) for 2 h., and after cooling, the solution is poured into 30% potassium carbonate solution (50 mL) and extracted with methylene chloride. The organic extracts are dried ($Na_2SO_4$) and concentrated to give colorless crystals (18 g). This material is dissolved in methanol (50 mL) and combined with a methanolic solution (10 mL) of fumaric acid (17.8 g). Isopropanol is added (150 mL) and the mixture concentrated on a hot plate to a volume of 50 mL. Upon cooling, crystals of the fumarate salt are collected (33.1 g, %, m.p. 166–167° C.)

EXAMPLE 2

2-Keto-5 6-benzomorpholine (4-azachroman-3-one)

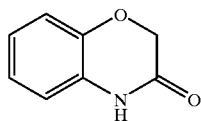

A mixture of 2-nitrophenol (47.92 g, 0.34 mol), ethyl bromoacetate (50.1 g, 0.3 mol) and potassium carbonate (96 g, 0.7 mol) in dimethyl formamide (200 mL) is heated at 80° C. for 22 h., cooled, poured into water (500 mL), and extracted with ether (2×250 mL). The combined organic extracts are washed once with water, dried and concentrated to give an orange oil which crystallizes upon standing.

A portion of the crystals (15 g) is dissolved in ethanol (120 mL) and hydrogenated over 10% Pd/C at 40 PSI $H_2$ for 6 h. The resulting heterogeneous mixture is filtered through celite and concentrated to give 9.49 g of grey crystals (m.p. 163–164° C.).

EXAMPLE 3

3-(1-[4-{(4-Pyrimidin-2-yl)piperazin-1-yl}]butyl) amino-2H-1,4-benzoxazine difumarate (Compound 1)

A solution of 2-keto-5,6-benzomorpholine (4-azachroman-3-one, 521 mg) and trimethyloxonium tetrafluoroborate (590 mg) in 50 mL of dry pentene stabilized chloroform is stirred at room temperature overnight. To this mixture is added a solution of 1-(pyrimidin-2-yl)-4-(4-aminobutyl)piperazine (822 mg) and triethylamine (5 mL) and the resultant solution refluxed overnight under nitrogen. After cooling, the solution is concentrated and partitioned between water and ethyl acetate and the organic layer is dried and concentrated to give a brown oil. Purification using preparative thin layer chromatography on silica eluting with 10% $CH_3OH$, 89% $CHCl_3$, 1% $NH_4OH$ provides the product as a colorless oil (340 mg, $R_f$=0.52). This material is combined with 215 mg of fumaric acid in 5 mL of methanol. Isopropanol (20 mL) is added and the solution volume reduced to approximately 5 mL on a hot plate. Upon cooling, the product (alternatively named 4-azachroman-3-yl(4-(4-pyrimidin-2-ylpiperazinyl)butyl)amine, 305 mg, m.p. 169–171° C.) is collected by filtration.

EXAMPLE 4

3-(1-[3-{(4-Pyrimidin-2-yl)piperazin-1-yl}]propyl) amino-2H-1,4-benzothiazine (Compound 4)

A solution of commercially available 2-keto-5,6-benzothiomorpholine (1,3,4-trihydro-4-thiaquinolin-2-one, 500 mg, 3 mmol) and trimethyloxonium tetrafluoroborate (480 mg, 3.3 mmol) in 50 mL of dry pentene stabilized chloroform is stirred at room temperature overnight. To this is then added 1-(pyrimidin-2-yl)-4-(3-aminopropyl) piperazine (1.36 g) and triethylamine (5 mL) and the resultant solution refluxed overnight under nitrogen. After cooling, the solution is concentrated and partitioned between water and ethyl acetate. The organic layer is dried and concentrated to give a brown oil which is purified using preparative thin layer chromatography on silica eluting with 10% $CH_3OH$, 89% $CHCl_3$, 1% $NH_4OH$ to provide the product as a yellow oil (500 mg, $R_f$=0.31). This material is combined with 315 mg of fumaric acid in 5 mL of methanol. Isopropanol (20 mL) is added and the solution reduced to a volume of approximately 5 mL on a hot plate. Upon cooling, the product (alternatively named, ((3-(4-pyrimidin-2-ylpiperazinyl)propyl)-2-1,2,3,4-tetrahydro-4-thiaquinolylamine, 480 mg, m.p. 212–213° C.) is collected by filtration.

EXAMPLE 5

The following compounds are prepared essentially according to the procedures set forth above in Examples 1–4.

(a) 3-(1-[2-{(4-Pyrimidin-2-yl)piperazin-1-yl}]ethyl) amino-2H-1,4-benzoxazine fumarate (m.p. 169–171° C., Compound 7)

(b) 3-(1-[3-{(4-Pyrimidin-2-yl)piperazin-1-yl}]propyl) amino-2H-1,4-benzoxazine fumarate (m.p. 179–181° C., Compound 8)

(c) 3-(1-[4-{(4-Pyrimidin-2-yl)piperazin-1-yl}]butyl) amino-2H-1,4-benzoxazine fumarate (m.p. 180–181° C., Compound 9)

(d) 3-(1-[3-{(4-Pyridin-2-yl)piperazin-1-yl}]propyl) amino-2H-1,4-benzoxazine fumarate (Compound 10)

(e) 3-(1-[3-{4-Phenylpiperazin-1-yl}]propyl)amino-2H-1,4-benzoxazine fumarate (Compound 3)

(f) 3-(1-[2-{(4-[5-Fluoropyrimidin-2-yl])piperazin-1-yl}] ethyl)amino-2H-1,4-benzoxazine fumarate (m.p. 163–164° C., Compound 6)

(g) 3-(1-[3-{(4-[5-Fluoropyrimidin-2-yl])piperazin-1-yl}]propyl)amino-2H-1,4-benzoxazine fumarate (m.p. 179–180° C., Compound 11)

(h) 3-(1-[4-{(4-[5-Fluoropyrimidin-2-yl])piperazin-1-yl}]butyl)amino-2H-1,4-benzoxazine fumarate (m.p. 144–154° C., Compound 12)

(i) 3-(1-[4-{(4-[5-Methylpyrimidin-2-yl])piperazin-1-yl}]butyl)amino-2H-1,4-benzoxazine hydrobromide (m.p. 278–279° C., Compound 13)

(j) 3-(1-[2-{(4-Pyrimidin-2-yl)piperazin-1-yl}]ethyl)amino-2H-1,4-benzothiazine fumarate (m.p. 169–171° C., Compound 14)

(k) 3-(1-[4-{(4-Pyrimidin-2-yl)piperazin-1-yl}]butyl)amino-2H-1,4-benzothiazine (m.p. 182–183° C., Compound 15)

(l) Benzo[b]morpholin-3-ylmethyl[4-(4-pyrimidin-2-ylpiperazinyl)butyl]amine (Compound 2; alternate name: 3-(N-[4-{(4-Pyrimidin-2-yl)piperazin-1-yl}]butyl)-N-methylamino-2H-1,4-benzoxazine)

(m) Benzo[b]morpholin-3-yl[2-(4-(2-pyridyl)piperazinyl)ethyl]amine (Compound 5; alternate name: 3-(1-[2-{(4-[Pyrid-2-yl])piperazin-1-yl}]ethyl)-amino-2H-1,4-benzoxazine)

EXAMPLE 6

Assay for $D_2$ and $D_4$ Receptor Binding Activity

Pellets of COS cells containing recombinantly produced $D_2$ or $D_4$ receptors from African Green monkey are used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is again centrifuged as described above and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 (Nemonapride, cis-5-Chloro-2-methoxy-4-(methylamino)-N-(2-methyl-2-(phenylmethyl)-3-pyrrolidinyl)benzamide)and the test compound in a total incubation of 1.0 ml. Nonspecific binding is defined as that binding found in the presence of 1 mM spiperone; without further additions, nonspecific binding is less than 20% of total binding. Binding characteristics of examples of the invention for the $D_2$ and $D_4$ receptor subtypes are shown in Table 2 for rat striatal homogenates.

TABLE 2

| Compound Number[1] | $D_4$ $K_i$ (nM) | $D_2$ $K_i$ (nM) |
|---|---|---|
| 1 | 4 | >1000 |
| 4 | 10 | >100 |
| 6 | 182 | >100 |

The above compound numbers relate to compounds shown in Table 1. The compounds tested are the compounds described in the above examples. In all cases, test compounds are acid addition salts.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

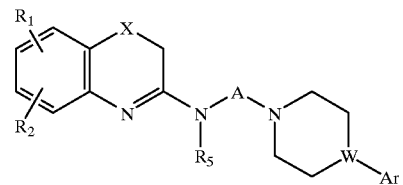

or the pharmaceutically acceptable acid addition salts thereof, wherein:

Ar represents aryl or heteroaryl of the formula

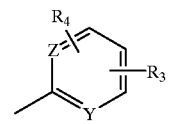

where Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, cycloalkoxy, alkylthio, hydroxy, amino, mono- or dialkylamino where each alkyl is $C_1$–$C_6$ alkyl, cyano, nitro, trifluoromethyl or trifluoromethoxy; or $R_3$ and $R_4$ together represent $C_1$–$C_2$ alkylene dioxy or $C_1$–$C_3$ alkylene oxy;

$R_5$ is hydrogen or $C_1$–$C_6$ alkyl;

W, Y and Z independently represent CH or nitrogen;

X is oxygen or sulfur; and

A represents an alkylene group of 2 to 5 carbon atoms each of which carbon atoms is optionally substituted with one or two alkyl groups having from 1 to 4 carbon atoms.

2. A compound according to claim 1, wherein $R_5$ is hydrogen, methyl, or ethyl.

3. A compound of the formula:

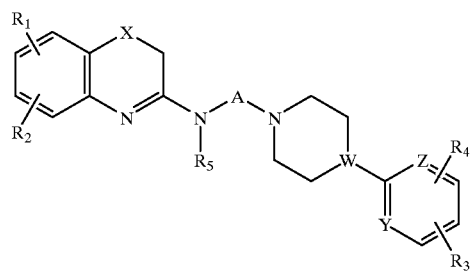

or the pharmaceutically acceptable salts thereof, wherein:

Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, alkylthio, hydroxy, amino, mono- or dialkylamino where each alkyl is $C_1$–$C_6$ alkyl, cyano, nitro, trifluoromethyl or trifluoromethoxy;

$R_5$ is hydrogen or $C_1$–$C_6$ alkyl;

W represents CH or nitrogen;

X is oxygen or sulfur; and

A represents an alkylene group of 2 to 5 carbon atoms each of which carbon atoms is optionally substituted with one or two alkyl groups having from 1 to 4 carbon atoms.

4. A compound according to claim 3 where Z and Y are both nitrogen.

5. A compound according to claim 4, where $R_1$ and $R_2$ are hydrogen and $R_5$ is hydrogen, methyl, or ethyl.

6. A compound of the formula:

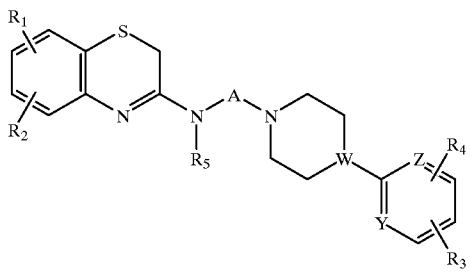

or the pharmaceutically acceptable salts thereof, wherein:

Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, alkylthio, hydroxy, amino, mono- or dialkylamino where each alkyl is $C_1$–$C_6$ alkyl, cyano, nitro, trifluoromethyl or trifluoromethoxy;

$R_5$ is hydrogen or $C_1$–$C_6$ alkyl;

W represents CH or nitrogen; and

A represents an alkylene group of 2 to 5 carbon atoms each of which carbon atoms is optionally substituted with one or two alkyl groups having from 1 to 4 carbon atoms.

7. A compound according to claim 6, wherein Z and Y are both nitrogen.

8. A compound according to claim 7, wherein W, Y and Z are nitrogen, $R_5$ is hydrogen, methyl, or ethyl, and $R_1$ and $R_2$ are both hydrogen.

9. A compound of the formula:

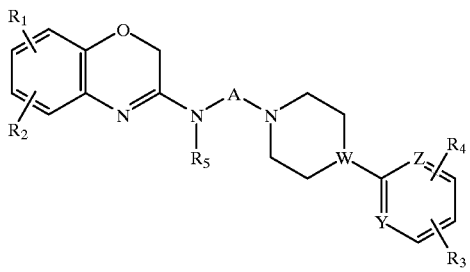

or the pharmaceutically acceptable salts thereof, wherein:

Y and Z independently represent CH or nitrogen;

$R_1$, $R_2$, $R_3$ and $R_4$ are the same or different and represent hydrogen, halogen, $C_1$–$C_6$ alkyl, $C_1$–$C_4$ alkoxy, alkylthio, hydroxy, amino, mono- or dialkylamino where each alkyl is $C_1$–$C_6$ alkyl, cyano, nitro, trifluoromethyl or trifluoromethoxy;

$R_5$ is hydrogen or $C_1$–$C_6$ alkyl;

W represents CH or nitrogen; and

A represents an alkylene group of 2 to 5 carbon atoms each of which carbon atoms is optionally substituted with one or two alkyl groups having from 1 to 4 carbon atoms.

10. A compound according to claim 9, wherein Z and Y are both nitrogen.

11. A compound according to claim 9, wherein W, Y and Z are nitrogen, $R_5$ is hydrogen, methyl, or ethyl, and $R_1$ and $R_2$ are both hydrogen.

12. A compound according to claim 1, which is 3-(1-[2-{(4-Pyrimidin-2-yl)piperazin-1-yl}]ethyl)amino-2H-1,4-benzoxazine.

13. A compound according to claim 1, which is 3-(1-[3-{(4-Pyrimidin-2-yl)piperazin-1-yl}]propyl)amino-2H-1,4-benzoxazine.

14. A compound according to claim 1, which is 3-(1-[4-{(4-Pyrimidin-2-yl)piperazin-1-yl}]butyl)amino-2H-1,4-benzoxazine.

15. A compound according to claim 1, which is 3-(1-[3-{(4-Pyridin-2-yl)piperazin-1-yl}]propyl)amino-2H-1,4-benzoxazine.

16. A compound according to claim 1, which is 3-(1-[3-{4-Phenylpiperazin-1-yl}]propyl)amino-2H-1,4-benzoxazine.

17. A compound according to claim 1, which is 3-(1-[2-{(4-[5-Fluoropyrimidin-2-yl])piperazin-1-yl}]ethyl)amino-2H-1,4-benzoxazine.

18. A compound according to claim 1, which is 3-(1-[3-{(4-[5-Fluoropyrimidin-2-yl])piperazin-1-yl}]propyl)amino-2H-1,4-benzoxazine.

19. A compound according to claim 1, which is 3-(1-[4-{(4-[5-Fluoropyrimidin-2-yl])piperazin-1-yl}]butyl)amino-2H-1,4-benzoxazine.

20. A compound according to claim 1, which is 3-(1-[4-{(4-[5-Methylpyrimidin-2-yl])piperazin-1-yl}]butyl)amino-2H-1,4-benzoxazine.

21. A compound according to claim 1, which is -(1-[2-{(4-Pyrimidin-2-yl)piperazin-1-yl}]ethyl)amino-2H-1,4-benzothiazine.

22. A compound according to claim 1, which is 3-(1-[3-{(4-Pyrimidin-2-yl)piperazin-1-yl}]propyl)amino-2H-1,4-benzothiazine.

23. A compound according to claim 1, which is 3-(1-[4-{(4-Pyrimidin-2-yl)piperazin-1-yl}]butyl)amino-2H-1,4-benzothiazine.

24. A compound according to claim 1, which is 3-(N-[4-{(4-Pyrimidin-2-yl)piperazin-1-yl}]butyl)-N-methylamino-2H-1,4-benzoxazine.

25. A compound according to claim 1, which is 3-(1-[2-{(4-[Pyrid-2-yl])piperazin-1-yl}]ethyl)-amino-2H-1,4-benzoxazine.

26. A pharmaceutical composition comprising a compound according to claim 1, together with at least one pharmaceutically acceptable carrier or excipient.

27. A method for treatment of schizophrenia, psychotic depression, mania, Parkinson's disease, or tardive dyskinesia which comprises administration to a patient in need thereof an amount of a compound according to claim 1 sufficient to alter the symptoms presented by the patient.

28. A method for treatment of cognitive disorders, memory impairment, attention deficit disorder, or Alzheimer's disease which comprises administration to a patient in need thereof an amount of a compound according to claim 1 sufficient to alter the symptoms presented by the patient.

29. A method for treatment of the extrapyramidal side effects associated with the use of neuroleptic agents which comprises administration to a patient in need thereof an amount of a compound according to claim 1 sufficient to alter the symptoms presented by the patient.

* * * * *